(12) United States Patent
Nunez et al.

(10) Patent No.: US 10,525,180 B2
(45) Date of Patent: Jan. 7, 2020

(54) INTEGRATED SENSORS FOR INTRAVENTRICULAR VAD

(71) Applicant: HeartWare, Inc., Miami Lakes, FL (US)

(72) Inventors: Nathalie Jeannette Nunez, Doral, FL (US); Timothy McSweeney, South Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 218 days.

(21) Appl. No.: 15/695,529

(22) Filed: Sep. 5, 2017

(65) Prior Publication Data

US 2018/0064860 A1 Mar. 8, 2018

Related U.S. Application Data

(60) Provisional application No. 62/383,794, filed on Sep. 6, 2016.

(51) Int. Cl.
*A61M 1/10* (2006.01)

(52) U.S. Cl.
CPC .......... *A61M 1/107* (2013.01); *A61M 1/1086* (2013.01)

(58) Field of Classification Search
None
See application file for complete search history.

(56) References Cited

U.S. PATENT DOCUMENTS

| 7,083,588 | B1* | 8/2006 | Shmulewitz | A61M 1/3621 |
| | | | | 604/8 |
| 9,050,418 | B2 | 6/2015 | Schima et al. | |
| 9,173,984 | B2 | 11/2015 | LaRose et al. | |
| 9,579,432 | B2* | 2/2017 | Tamez | A61M 1/10 |
| 9,656,011 | B2* | 5/2017 | Graham | A61M 1/1036 |
| 9,662,431 | B2* | 5/2017 | Franano | A61M 1/3659 |
| 2008/0133006 | A1 | 6/2008 | Crosby et al. | |

(Continued)

FOREIGN PATENT DOCUMENTS

| WO | 9959652 A1 | 11/1999 |
| WO | 2014042925 A2 | 3/2014 |
| WO | 2016001284 A2 | 1/2016 |

OTHER PUBLICATIONS

International Search Report and Written Opinion dated Dec. 7, 2017 for corresponding International Application No. PCT/US2017/050078; International Filing Date: Sep. 5, 2017 consisting of 13-pages.

*Primary Examiner* — Brian T Gedeon
(74) *Attorney, Agent, or Firm* — Christopher & Weisberg, P.A.

(57) ABSTRACT

A ventricular assist device includes a pump including a housing having an inlet, an outlet and a moveable element disposed in the housing for urging blood from the inlet to the outlet. An outflow cannula having a proximal end attached to the pump housing, a distal end remote from the pump housing, an interior bore in communication with the outlet of the pump housing, and at least one outlet aperture communicating with the interior bore remote from the pump housing is included. At least one sensor mounted to the outflow cannula and configured to detect a parameter of blood flowing at least one from the group consisting of through the outflow cannula and about an exterior of the outflow cannula is included.

16 Claims, 9 Drawing Sheets

(56) References Cited

U.S. PATENT DOCUMENTS

| | | | |
|---|---|---|---|
| 2014/0073837 A1* | 3/2014 | Kerkhoffs | A61M 1/1086 600/16 |
| 2015/0335804 A1 | 11/2015 | Marseille et al. | |
| 2016/0015878 A1 | 1/2016 | Graham et al. | |
| 2016/0166746 A1 | 6/2016 | Andrus | |

* cited by examiner

INTEGRATED SENSORS FOR INTRAVENTRICULAR VAD

CROSS-REFERENCE TO RELATED APPLICATION

This application is related to and claims priority to U.S. Provisional Patent Application Ser. No. 62/383,794, filed Sep. 6, 2016, entitled INTEGRATED SENSORS FOR INTRAVENTRICULAR VAD, the entirety of which is incorporated herein by reference.

STATEMENT REGARDING FEDERALLY SPONSORED RESEARCH OR DEVELOPMENT n/a

TECHNICAL FIELD

The present invention relates to blood pumps usable as implantable ventricular assist devices and, more particularly, to an improved blood pump design with integrated sensors.

BACKGROUND

In certain diseased states, the heart lacks sufficient pumping capacity to maintain adequate blood flow to the body's organs and tissues. For example, conditions such as ischemic heart disease and hypertension may leave the heart unable to fill and pump efficiently. This condition, also called congestive heart failure, may lead to serious health complications, including respiratory distress, cardiac asthma, and even death. In fact, congestive heart failure is one of the major causes of death in the Western World.

This inadequacy of the heart can be alleviated by providing a mechanical pump, also referred to as a ventricular assist device ("VAD"), to supplement the pumping action of the heart. VADs may be used to assist the right ventricle, the left ventricle, or both. For example, a VAD may assist the left ventricle by mechanically pumping oxygenated blood from the left ventricle into the aorta.

U.S. Pat. Nos. 9,050,418; 9,173,984; U.S. Pub. No. 2016/0015878 ("the '878 publication) and U.S. application Ser. No. 14/962,511, the disclosures of which are hereby incorporated herein by reference, disclose certain axial flow blood pumps that can be used as ventricular assist devices. When implanted, these and other implantable pumps, typically have an inlet that communicates with a ventricle of a patient and an outlet that communicates with an aorta via an outflow cannula that extends through the ventricle and into the aorta. A pumping element typically resides within the heart and urges oxygenated blood from the ventricle to the aorta.

When implanted and in operation, it is desirable to monitor certain parameters to detect abnormal operating conditions and to determine how the pump affects an environment surrounding the pump. For example, flow information can be obtained directly via an ultrasonic flow sensor or indirectly via a pressure sensor. Such information can be used to provide feedback for control of the pump and to detect a blockage or a situation where the pump outpaces a ventricle's blood supply leading to a suction condition.

Certain existing VADs, such as the centrifugal VAD disclosed in U.S. Pub. No. 2008/0133006, are fitted with an ultrasonic flow sensor for determining parameters associated with blood flow into the VAD's pump. However, such sensors are limited to determining parameters associated with blood flowing into the VAD and are not capable of determining parameters associated with blood flowing out of the VAD and to the remainder of the patient's body. In addition, such sensors are typically located near the pump's impeller and only obtain characteristics of the blood near the impeller rather than at an appreciable distance from the impeller where localized effects are not present. Thus, despite considerable effort devoted to improvements of such VADs, still further improvement are desirable.

SUMMARY

In one aspect of the present application, a ventricular assist device includes a pump including a housing having an inlet, an outlet and a moveable element disposed in the housing for urging blood from the inlet to the outlet. An outflow cannula having a proximal end attached to the pump housing, a distal end remote from the pump housing, an interior bore in communication with the outlet of the pump housing, and at least one outlet aperture communicating with the interior bore remote from the pump housing is included. At least one sensor mounted to the outflow cannula and configured to detect a parameter of blood flowing at least one from the group consisting of through the outflow cannula and about an exterior of the outflow cannula is included.

In another aspect of this Embodiment, the interior bore of the cannula has a longitudinal axis extending longitudinally and the outflow cannula has a transverse wall extending transverse to the longitudinal axis, the at least one sensor being mounted to the transverse wall.

In another aspect of this Embodiment, the transverse wall is disposed adjacent the distal end, and the at least one outlet aperture is disposed proximal to the transverse wall.

In another aspect of this Embodiment, the outflow cannula defines a tapered tip at its distal end, and the at least one outlet aperture includes a plurality of outlet apertures disposed in the tapered tip and spaced circumferentially around the axis of the interior bore.

In another aspect of this Embodiment, the transverse wall intersects the longitudinal axis of the interior bore.

In another aspect of this Embodiment, the at least one sensor includes at least one from the group consisting of a pressure sensor and a flow sensor.

In another aspect of this Embodiment, the transverse wall defines a terminal end of the bore.

In another aspect of this Embodiment, the transverse wall is contoured to direct blood flow in a direction toward the at least one outlet aperture.

In another aspect of this Embodiment, the transverse wall is defined between an interior portion that defines an extent of the interior bore and an exterior portion that defines an extent of outflow cannula remote from the pump.

In another aspect of this Embodiment, the sensor is mounted to at one of the interior portion and exterior portion.

In another aspect of this Embodiment, the device includes an electrical conductor extending proximally and distally along the cannula, the at least one sensor being electrically connected to the electrical conductor.

In another aspect of this Embodiment, the device includes a base member connected to the pump housing by an elongate member configured to form a gap therebetween.

In another aspect of this Embodiment, the outflow cannula further includes a sidewall surrounding the interior bore over at least a portion of its length, a least one said sensor being mounted to the sidewall.

In another aspect of this Embodiment, the at least one sensor includes at least one ultrasonic transducer mounted to the cannula, and wherein ultrasonic waves transmitted and received by the ultrasonic transducer, travel through the interior bore with a component of velocity in at least one of the proximal and distal directions.

In another aspect of this Embodiment, the at least one ultrasonic transducer includes two ultrasonic transducers spaced proximally and distally from one another.

In another aspect of this Embodiment, the at least one ultrasonic transducer includes a distal transducer mounted to the cannula adjacent the distal end thereof, and at least one of the pump and the cannula defines a reflective surface adjacent the proximal end of the cannula.

In another Embodiment, a method of assisting a pumping action of a heart includes operating a pump of a ventricular assist device to urge blood from an inlet of a pump housing to at least one outlet aperture of an outflow cannula connected to an outlet end of the pump housing. The outflow cannula has a bore in communication with an outlet of the pump housing and with the at least one outlet aperture. A parameter prevailing within the bore is sensed.

In another aspect of this Embodiment, the sensing the parameter prevailing within the bore includes sensing pressure imposed by blood flowing through the bore.

In another aspect of this Embodiment, the sensing the parameter prevailing within the bore includes transmitting an electronic signal indicative of the sensed parameter through one or more conductors.

In yet another Embodiment, a ventricular assist device includes a pump including a housing having an inlet, an outlet and a moveable element disposed in the housing for urging blood from the inlet to the outlet. An outflow cannula having a proximal end attached to the pump housing, a distal end remote from the pump housing, an interior bore in communication with the outlet of the pump housing, and at least one outlet aperture communicating with the interior bore remote from the pump housing is included. At least one sensor is mounted to the outflow cannula, the interior bore of the outflow cannula having an axis extending longitudinally, and the outflow cannula having a transverse wall extending transverse to the axis, the at least one sensor being mounted to the transverse wall and configured to detect a parameter of blood flowing at least one from the group consisting of through the outflow cannula and about an exterior of the outflow cannula. The at least one sensor includes at least one ultrasonic transducer mounted to the cannula and ultrasonic waves transmitted and received by the ultrasonic transducer, travel through the bore with a component of velocity in at least one of the proximal and distal directions. An electrical conductor extending proximally and distally along the cannula is included, the at least one sensor being electrically connected to the conductor.

BRIEF DESCRIPTION OF THE DRAWINGS

The features, aspects, and advantages of the present invention will become better understood with regard to the following description and accompanying drawings in which.

DETAILED DESCRIPTION

Figure 1A:
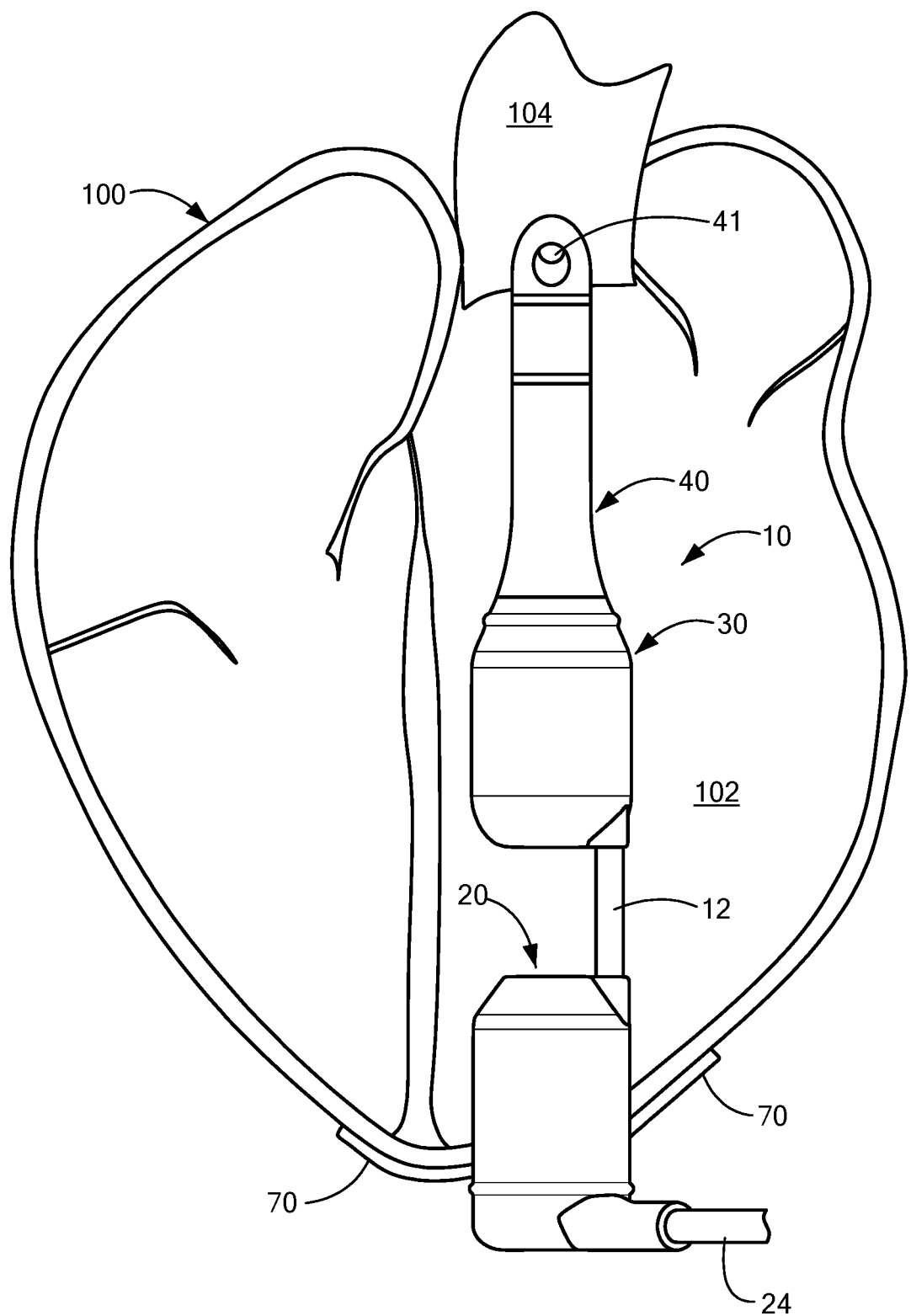
FIG. 1A is an elevational view of a VAD according to one embodiment of the present disclosure as implanted within a heart which is schematically represented.
Figure 1B:
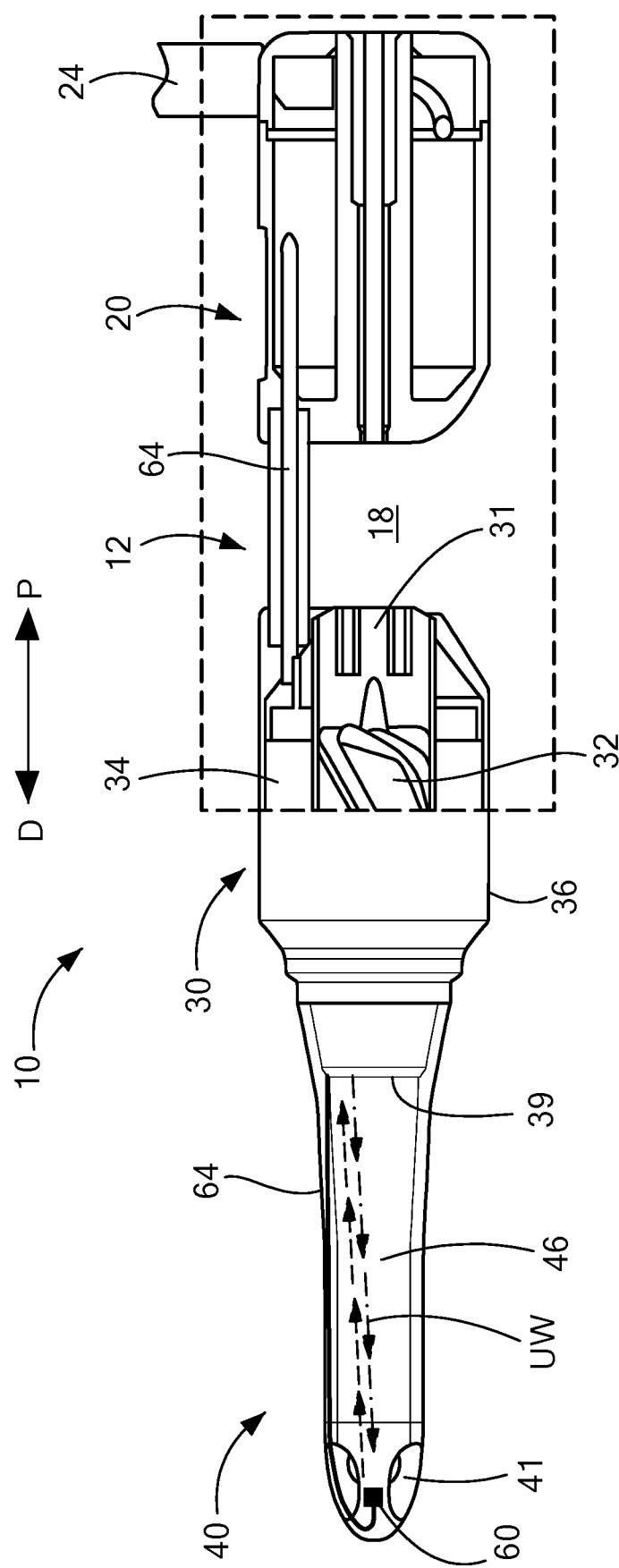
FIG. 1B is a partial cutaway and partial transparent view of the VAD of FIG. 1A.
Figure 1C:
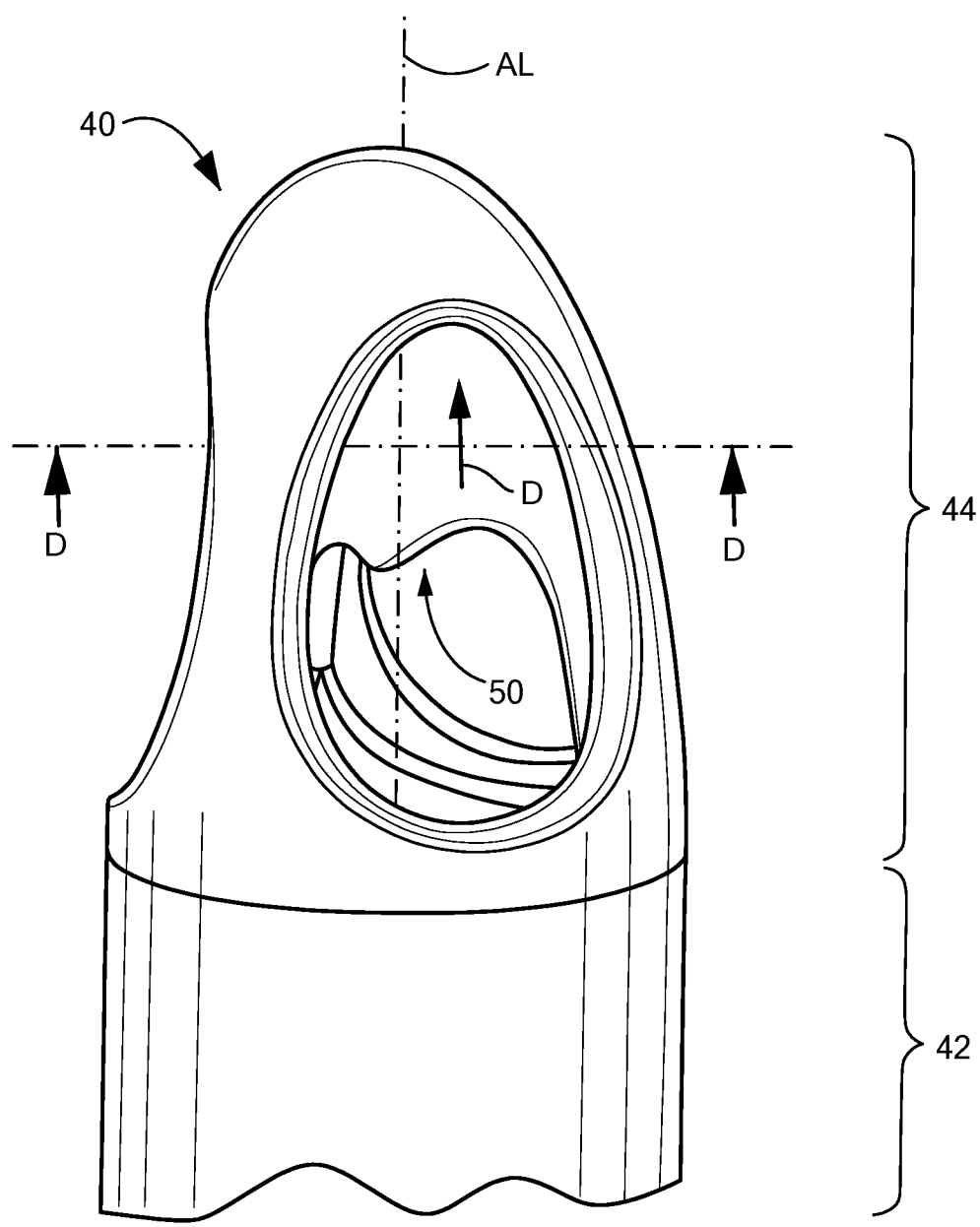
FIG. 1C is a fragmentary perspective view of a cannula of the VAD of FIG. 1.

Referring now to the drawings in which like designators refer to like elements, there is shown in FIGS. 1A-1F an intraventricular, axial flow VAD "10" according to an embodiment of the application. VAD 10 includes a pump 30 comprised of a pump housing 36 and internal components disposed within pump housing 36. Such internal components, as shown in FIG. 1B, include a moveable element or impeller 32 and electrical coils 34 for moving movable element 32 within pump housing 36. Pump housing 36 houses the internal components and defines an inlet 31 at a proximal end and an outlet 39 at a distal end thereof.

The VAD 10 further includes a base member or pedestal 20. Base member 20 is configured to be engaged by mounting ring 70 mounted to an outside of heart 100, as depicted in FIG. 1A. For example, mounting ring 70 may grip an outer surface 25 of base member 20 or by some other engagement means as is known in the art. An electric cable 24 extends from base member 20 in a direction transverse to a proximal-distal direction which is indicated by the arrow D-P in FIG. 1B. Electrical cable 24, when implanted, may communicate transcutaneously with an external power source and controller (not shown), such as via a driveline cable or a transcutaneous energy transfer system ("TET"). Alternatively, electrical cable 24, when implanted, may communicate with an internal controller (not shown) also implanted within the patient.

A strut or spacer element 12 mechanically connects base member 20 and pump 30. Such strut 12 is connected to an inlet end or proximal end of pump housing 26 and an inlet facing end or distal end of base member 20. Such connection between strut 12, base member 20 and pump 30 forms a gap 18 between base member 20 and pump 30 through which blood flows prior to entering inlet 31 of pump 30. Electrical conductors 64 from cable 24 extend through base member 20 and through strut 12 to pump 30.

Figure 1D:
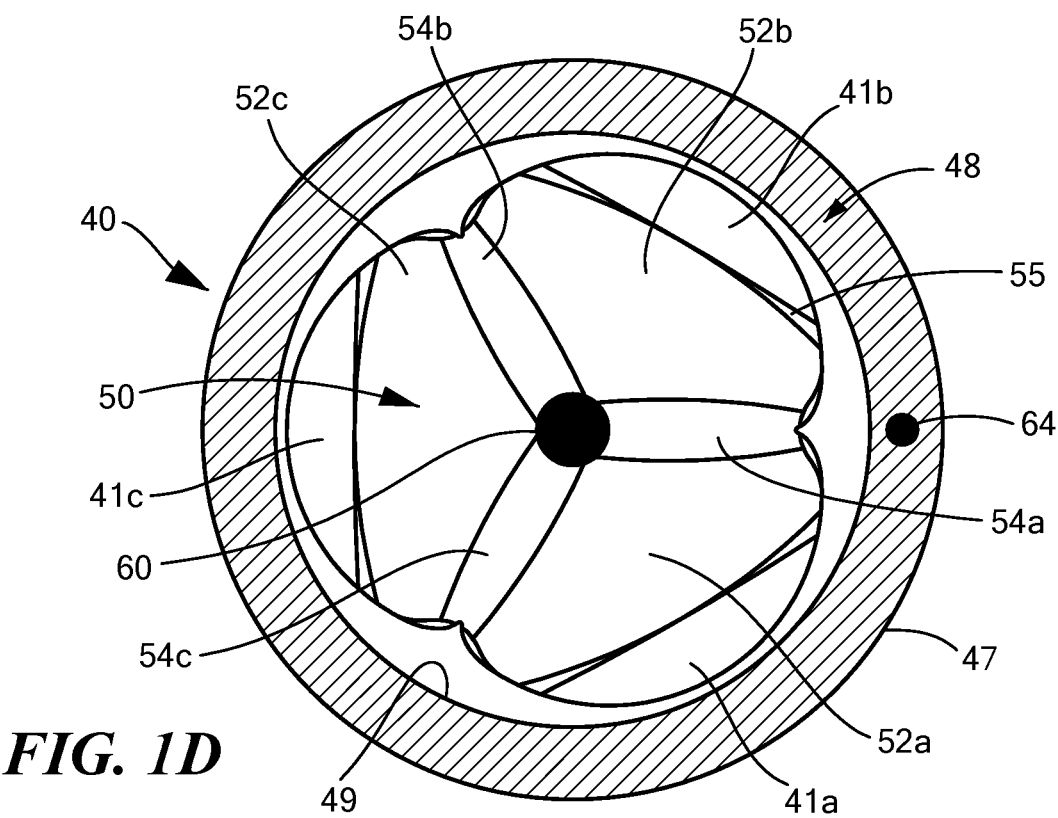
FIG. 1D is a sectional view taken along line D-D in FIG. 1B.
Figure 1E:
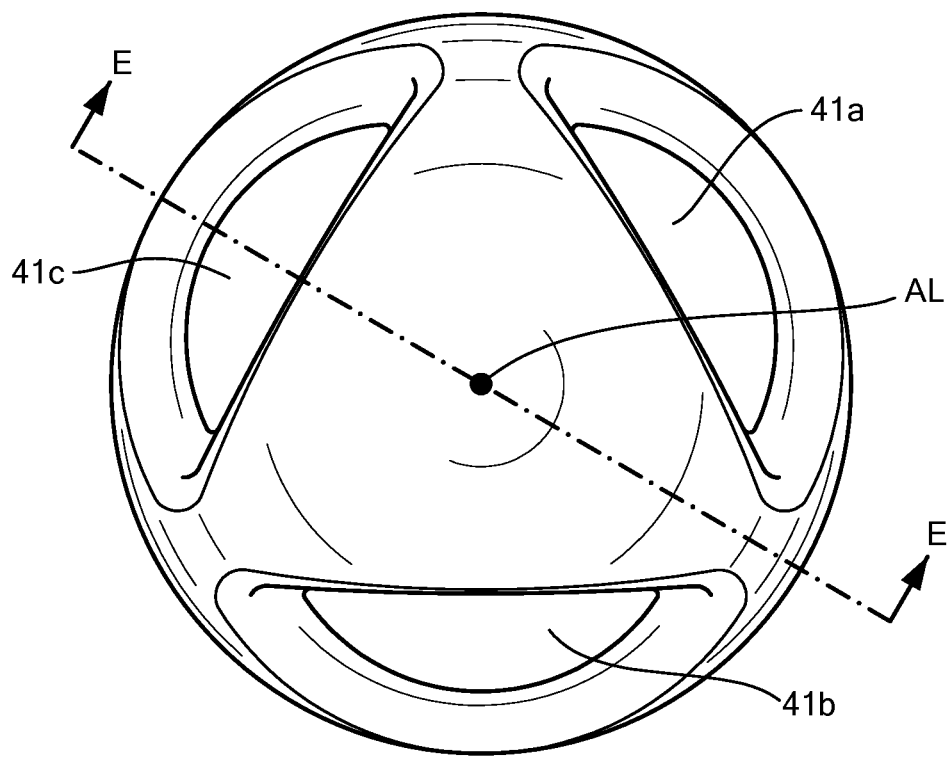
FIG. 1E is a top view of the cannula of FIG. 1B.

VAD 10 further includes an outflow cannula 40 connected to an outlet end of pump 30 and projects distally therefrom. Outflow cannula 40 includes a proximal portion 42 and a distal portion 44 connected to the proximal portion 42 (best shown in FIG. 1C). Outflow cannula 10 also includes a cannula sidewall 48 extending along its length. Cannula sidewall 48 is defined by an inner face 49 and outer face 47 as best seen in FIG. 1D. Sidewall 48 surrounds a bore 46 of cannula 40. Bore 46 defines a bore axis AL that extends in the proximal-distal direction along the length of cannula 40.

Distal portion 44, as shown, forms a closed-end, tapered tip of outflow cannula 40. Distal portion 44 also defines a plurality of outflow apertures 41 extending in a substantially radial direction through sidewall 48. In the particular embodiment depicted, distal portion 44 defines three outlet apertures 41*a*-*c*. However, more or less apertures are contemplated.

Figure 1F:
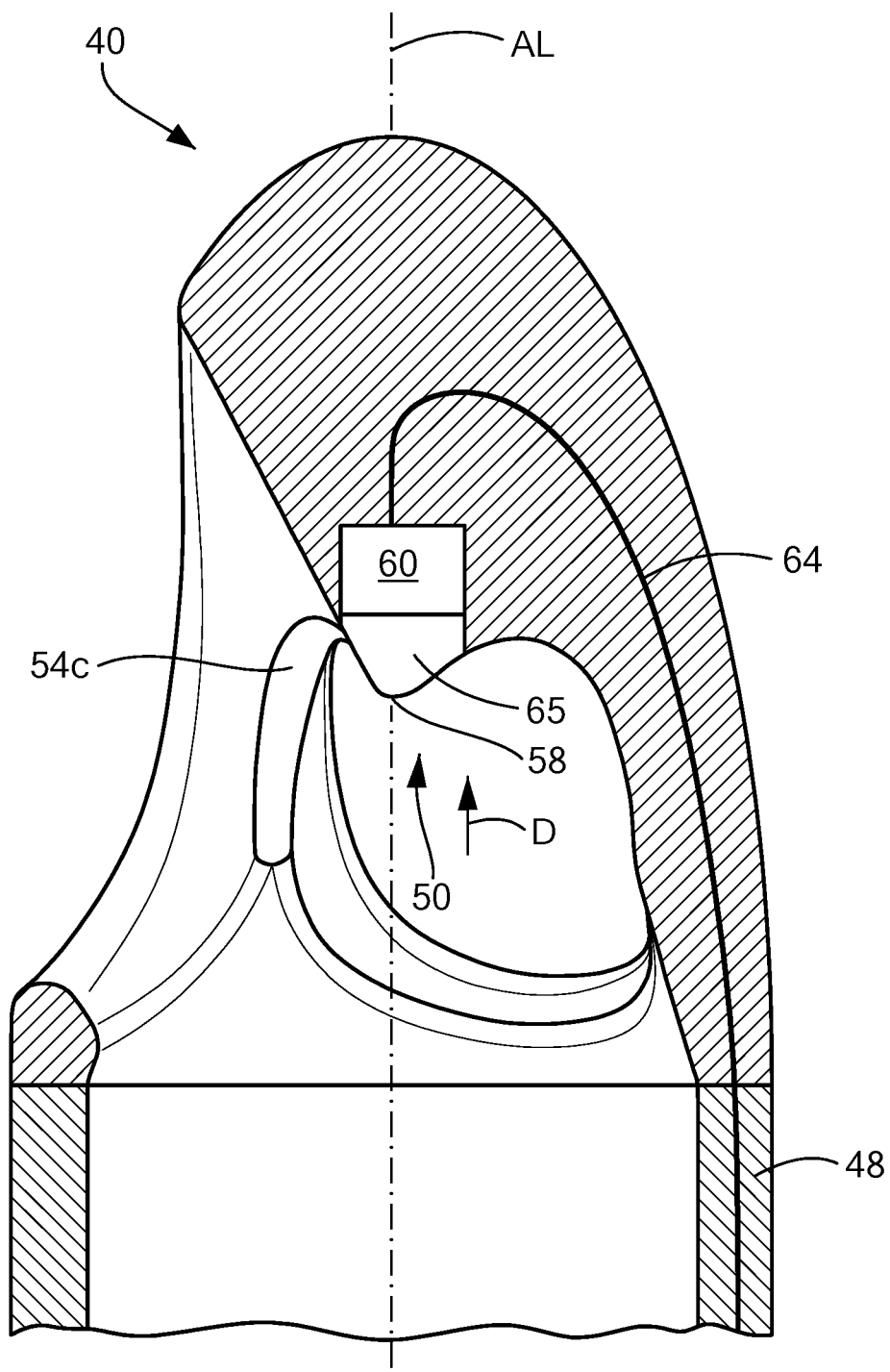
FIG. 1F is a sectional view taken along line F-F of FIG. 1D.

Distal portion 44 includes a transverse wall 50 that extends in a direction transverse to the bore axis AL and between opposite sides of sidewall 48, such that transverse wall 50 intersects the bore axis AL. In addition, transverse wall 50 defines a terminal end of bore 46 and is positioned substantially more distal than outflow apertures 41*a*-*c*. Transverse wall 50, as best shown in FIG. 1D, is preferably contoured to help direct blood flowing through bore 46 to outflow apertures 41*a*-*c*. In the particular embodiment depicted, transverse wall 50 includes bounding surfaces 52*a*-*c* that each have an outer portion 55 partially defining a distal end of a corresponding outlet aperture 41*a*-*c*. Bounding surfaces 52*a*-*c* extend inwardly from their respective outer portions 55 and intersect each other to form partial arches 54*a*-*c*. These partial arches 54*a*-*c* form an apex 58 which may be intersected by the bore axis AL, as seen in FIG. 1F. Although the embodiment depicted is contoured in the manner described, it should be understood that other configurations of transverse wall 50 are contemplated. For example, transverse wall 50 can be convexly or concavely dome shaped or substantially planar.

A sensor element 60 is mounted to transverse wall 50. In this embodiment, sensor element 60 is an ultrasonic transducer disposed within transverse wall 50. In this regard, ultrasonic transducer 60 may be positioned so as to be intersected by the bore axis AL and so that ultrasonic emissions are directed in a proximal direction opposite the blood flow direction D and along the bore axis AL toward the outlet 39 of pump 30. Ultrasonic transducer 60 can be alternatively positioned within transverse wall 50 so that ultrasonic emissions therefrom are directed across the bore axis AL and toward the outlet end of pump housing 36 or a reflective surface disposed on inner face 49 of cannula 40. Ultrasonic transducer 60 is configured to emit ultrasonic waves as well as receive reflected ultrasonic waves from pump 30 or inner face 49 of the outflow cannula. Ultrasonic transducer 60 can be any conventional transducer such as a conventional piezoelectric element that is configured to emit ultrasonic waves upon application of an alternating voltage at ultrasonic frequency and to provide an alternating electric potential when ultrasonic vibrations impinge on it.

Transducer 60 may be covered by a covering 65 that helps house and protect transducer 60 while allowing ultrasonic waves to pass therethrough unimpeded. Covering 65 may be molded or otherwise shaped to form pointed apex 58 of transverse wall 50, as depicted in FIG. 1F. However, covering 65 could alternatively be a flat piece of material orthogonally disposed relative to bore axis AL and intersected by partial arches 54*a*-*c*.

A conductor 64 is electrically connected to sensor element 60 and extends through transverse wall 50 and sidewall 48 of outflow cannula 40. Conductor 64 may terminate at the proximal end of cannula 40 with an electrical contact (not shown) which may be in conductive contact with an electrical contact on pump housing 30 for receiving power and transmitting signals when cannula 40 is connected to pump housing 30. Alternatively, conductor 64 may extend entirely through cannula 40, pump housing 30, strut 12, and pedestal 20 to cable 24 as depicted in FIG. 1B. The conductor 64 is connected through these connections to a signal processing apparatus (not shown) arranged to provide an electrical drive signal to the transducer; to receive electrical signals from the transducer; and to determine the flow velocity of blood in the cannula, and thus derive an estimate of flow rate through the cannula.

Outflow cannula 40 may be made from a polymer material in which the polymer is molded over transducer 60, conductor 64 and covering 65. Such polymer is preferably flexible to allow cannula 40 to adjust to the curvature of a mammalian subject's aorta. However, outflow cannula 40 can also be made from a ceramic or metallic material in which a recess for transducer 60 and covering 65 and a passageway for conductor 64 are formed therein so that such elements can be installed in the cannula 40.

When cannula 40 is connected to pump housing 36, distal portion 44 and sensor element 60 mounted thereto are disposed remote from pump outlet 39. Bore 46 communicates with outlet 39 and outlet apertures 41*a*-*c*. In this regard, bore 46 is disposed intermediate pump outlet 39 and outlet apertures 41*a*-*c*. The length of cannula 40 is such that cannula 40 extends into a mammalian subject's aorta 104 while base member 20 is connected to an apex of the heart 100 and pump 30 is located in the mammalian subject's ventricle 102. Cannula and bore may be curved or bendable to conform to aorta 104.

In a method of use, VAD 10 may be transapically implanted into a heart 100 of a mammalian subject as described in the aforementioned '878 publication. As implanted, outflow apertures 41*a*-*c* of outflow cannula 40 are positioned within an aorta 104. In addition, pump 30 and a portion of base member 20 are disposed within a left ventricle 102 as depicted in FIG. 1A. Base member 20 may be secured to an apex of heart 100 via a mounting ring 70 or some other securement device.

When pump 30 is powered on, sensor element 60 may also be powered on, and blood flows into inlet 31 of pump housing 36 through gap 18. Moveable element 32 urges this blood into bore 46 of outflow cannula 40 and helps propel the blood through outlet apertures 41*a*-*c* into aorta 104. Sensor element 60 emits ultrasonic waves UW, as shown in FIG. 1B. Such waves are reflected by a reflective surface either on pump housing 36 or inner face 46 of outlet cannula 40 and projected back to sensor element 60 with a component of velocity in a distal direction toward sensor element 60. Sensor element 60 receives the reflected waves and generates an electric signal indicative of the flow conditions of the blood flowing through bore 46.

Because the two-way path from transducer 60 to the reflective surface and back to transducer 60 has components parallel to the direction of blood flow, the time of flight of the ultrasonic waves UW is influenced by the velocity of the blood according to the well-known Doppler effect. This effect causes the phase of the ultrasonic waves UW received by sensor element 60 to vary with the blood velocity and, thus, with the flow rate. The mathematical relationships used to convert phase difference to flow velocity and to convert flow velocity to flow rate, are well known. In this regard, flow rate is an average flow rate taken over the distance of the ultrasonic wave's travel. Thus, when the ultrasonic wave UW travels back and forth from transducer 60 at the distal end of cannula 40 to pump housing 36 at a proximal end of cannula 40, the determined flow rate is an average flow rate along the length of bore 46. Similarly, where cannula 40 is so curved that ultrasonic wave UW reflects off of inner face 49 of cannula 40 back to sensor element 60, the determined flow rate is an average flow rate taken along the distance between sensor element 60 and the reflective surface, which in this example is a distance shorter than the length of bore 46. Although the distance of travel for ultrasonic wave UW may vary from patient to patient based on their respective aortic curvature and the curvature of cannula 40 to correspond to such curvature, it should be understood that once cannula 40 is positioned in the patient's aorta, the cannula 40 is permanently set so that the distance of the reflective surface and sensor element 60 is substantially fixed so as to not appreciably affect the phase shift of the wave UW. Although this distance may not be immediately known upon implantation of VAD 10 as the curvature of cannula 40 may need to be adjusted during implantation, the signal processing apparatus can be calibrated to account for this unknown.

The electrical signals generated by sensor element 60 are transmitted through conductor 64 down to cable 24 which may further transmit these signals to the signal processing apparatus (not shown). The signal processing apparatus may be part of an external or internal controller which may further process the signals and store information derived therefrom for later retrieval or real-time display. Such information may allow a clinician and/or patient to continuously monitor prevailing conditions of blood as it is dispersed into the aorta from outflow cannula 40.

Figure 2:
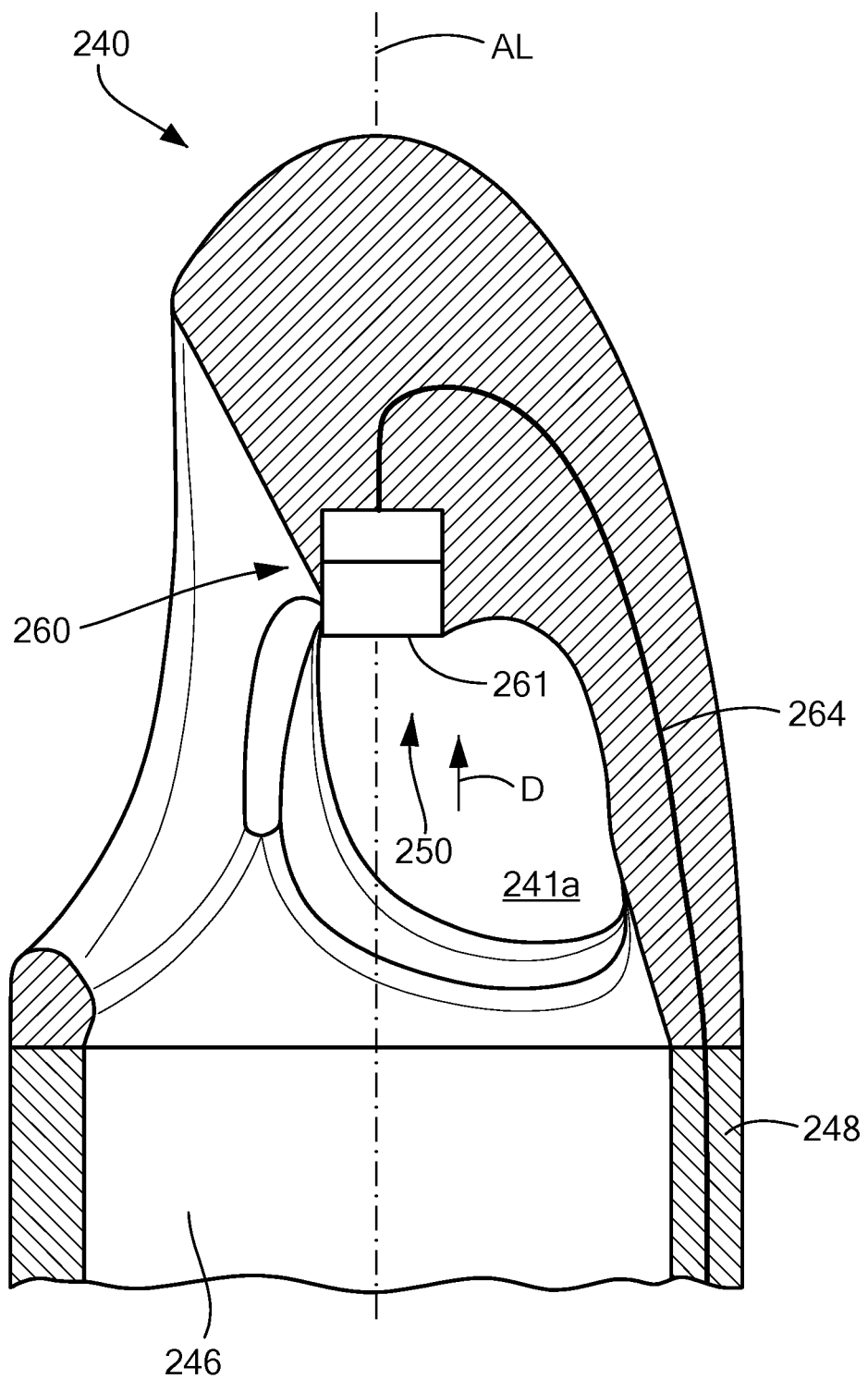
FIG. 2 is a sectional view of a cannula according to another embodiment of the present disclosure taken along a line intersecting an axis AL thereof.

Other alternative embodiments of the aforementioned devices are contemplated. For example, in one embodiment depicted in FIG. 2, VAD 10 may include outflow cannula 240 connected to pump housing 36. Outflow cannula 240 is similar to outflow cannula 40 with the difference being that a pressure sensor 260 is mounted thereto in lieu of ultrasonic transducer 60. As shown in FIG. 2, pressure sensor 260 may be any pressure sensor configured for use within the body of a mammalian subject and may include a sensing element 261 that senses mechanical inputs for conversion to electrical outputs. For example, pressure sensor 260 may be a microelectromechanical system (MEMS) with a built-in sensing element, such as a diaphragm, configured to sense blood pressure in-vivo. Pressure sensor 260 is mounted to transverse wall 250 so that sensing element 261 is located at the distal end of a bore 246 and is exposed to blood flowing therethrough. A conductor 264 for supplying power and transmitting signals is connected to pressure sensor 240 and extends through transverse wall 250 and sidewall 248 of the cannula 240.

In a method of use, when pump 30 is powered on, pressure sensor 260 may also be powered on. Blood is urged through bore 246 of cannula 240 toward outlet apertures 241a-b. Pressure sensor 260 senses the pressure of such blood when such blood reaches the end of bore 246 and just prior to exiting outflow apertures 241a-c into the aorta 104. Sensor 260 generates signals indicative of the pressure sensed by sensing element 261. Such signals are transmitted through conductor down to cable 24 which may further transmit these signals to an external or internal controller which may further process the signals and store information derived therefrom for later retrieval or real-time display. Such information may allow a clinician and/or patient to continuously monitor prevailing conditions of blood as it is dispersed into the aorta from outflow cannula 240.

Pressure sensor 260 located in transverse wall 250 near outflow apertures 241a-c is beneficial in that the pressure determined by such sensor closely approximates blood pressure within the aorta and, thus, mean arterial pressure ("MAP") of the mammalian subject. This allows pump 30 to be controlled for optimal tissue perfusion and also allows cannula to provide continuous or near continuous cardiac output monitoring without the need for sedation.

Figure 3:
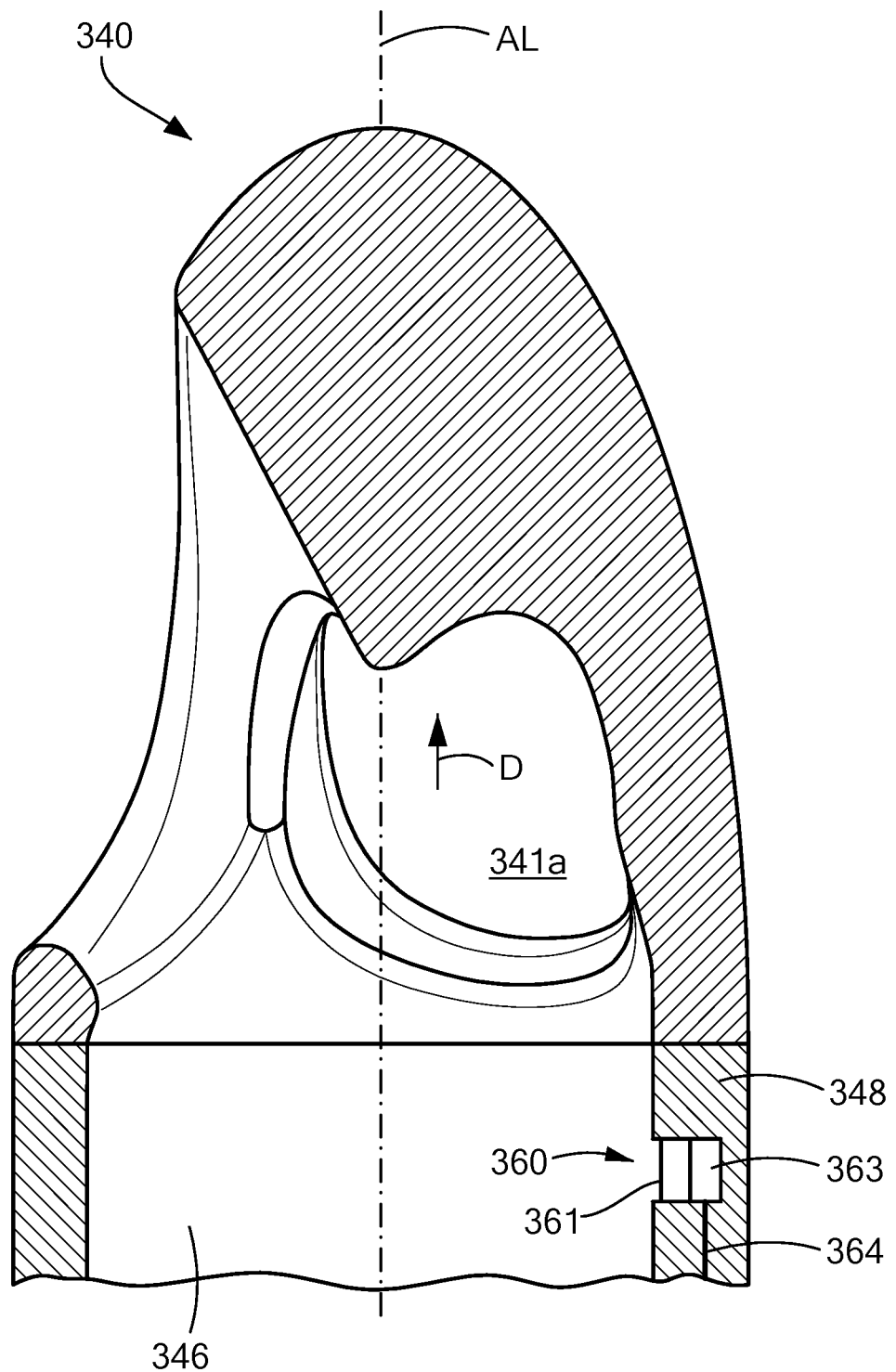
FIG. 3 is a sectional view of a cannula according to a further embodiment of the present disclosure taken along a line intersecting an axis AL thereof.

In another embodiment, as depicted in FIG. 3, an outflow cannula 340 is similar to outflow cannula 40 with the difference being that a pressure sensor 360 is mounted to a sidewall 348 thereof. Pressure sensor 360 may be similar to pressure sensor 260 and, as such, may include a sensing element 561. Sensor 360 is mounted to sidewall 348 offset from bore axis AL and so that sensing element 361 is exposed to blood flowing through the bore 346. This pressure sensor 360 can be mounted to sidewall 348 at any location along the length of cannula 340. For example, as shown in FIG. 3, pressure sensor 360 may be mounted closer to the outlet apertures 341a-b than the outlet 46 of the pump 30. In another example, sensor 360 may be mounted near or at the midpoint of the length of cannula 340. In a further example, sensor 360 may be mounted closer to outlet 46 of the pump than outlet apertures 351a-b. The Bernoulli principle can be utilized to estimate blood flow from the pressure measured by sensor 360 at each of these exemplary locations.

In a method of use, when pump 30 is powered on, sensor 360 may also be powered on. Blood is urged through the bore 346 of cannula 340 toward outlet apertures 341 a-c. Sensing element 361 senses the pressure of such blood as blood flows over sensor 360 and just prior to exiting outflow apertures 341a-c into the aorta 104. Sensor 360 generates signals indicative of the pressure sensed by sensing element 361. Such signals are transmitted through conductor 364 down to cable 24 which may further transmit these signals to an external or internal controller which may further process the signals and store information derived therefrom for later retrieval or real-time display. Such information may allow a clinician and/or patient to continuously monitor prevailing conditions of blood as it is dispersed into the aorta from outflow cannula 340.

Figure 4:
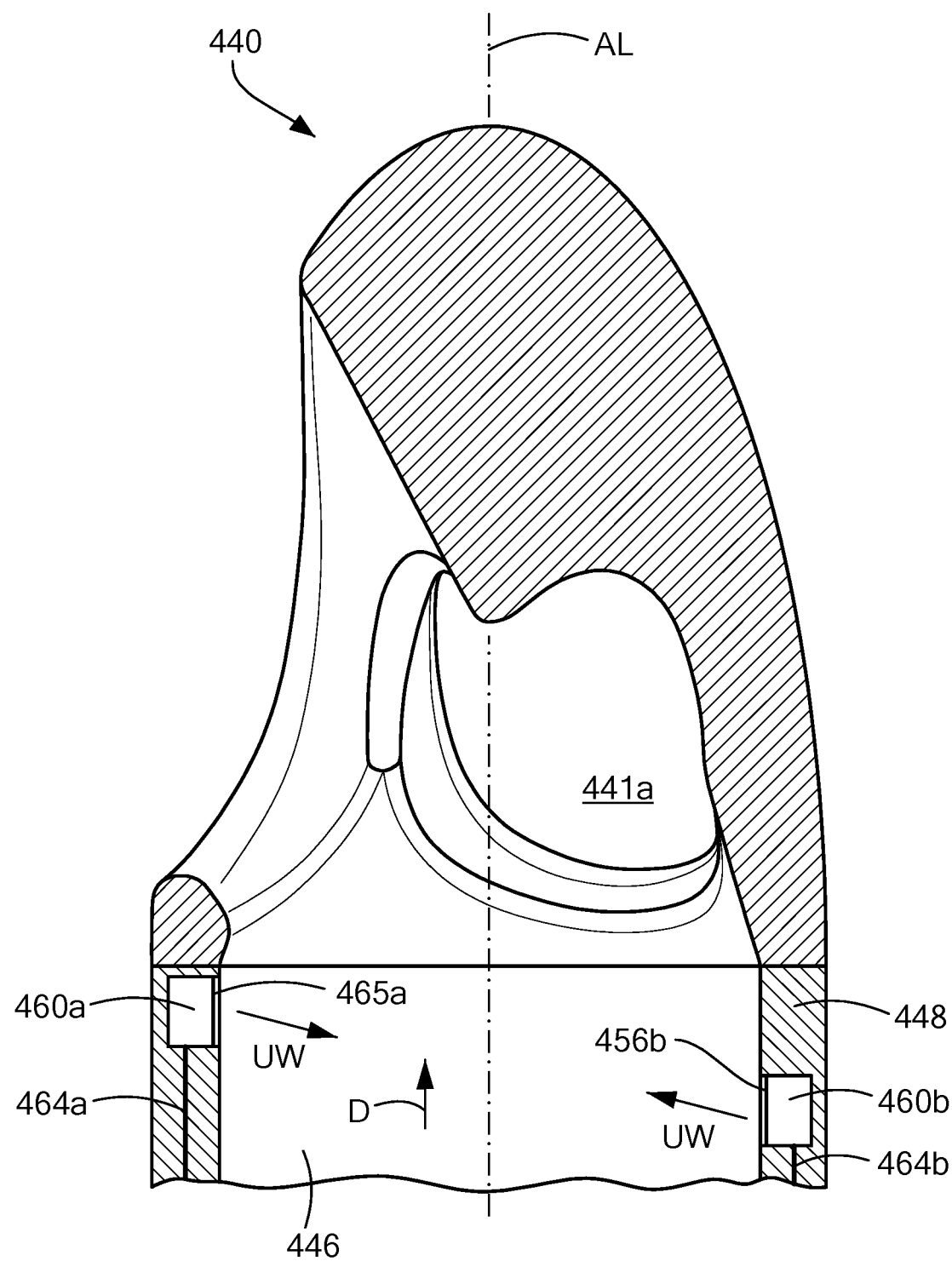
FIG. 4 is a sectional view of a cannula according to yet another embodiment of the present disclosure taken along a line intersecting an axis AL thereof.

In a further embodiment, as depicted in FIG. 4, an outflow cannula 440 is similar to outflow cannula 40 with the difference being that one or more ultrasonic transducers are mounted to sidewall 448 of outflow cannula 440. As shown, a first ultrasonic transducer 240a is mounted to sidewall 448 at a first location and a second ultrasonic transducer 460b is mounted to sidewall 448 at a second location. These locations are at opposite sides of the bore axis AL. In addition, first transducer 460a, as shown, is positioned more distal than second transducer 460b. However, in some embodiments, first transducer 460a may be more proximal than second transducer 460b. Thus, first and second transducers 460a-b are preferably positioned in offset locations along axis AL. In this regard, transducers 460a-b may be oriented within sidewall 448 so that ultrasonic waves UW are directed from one transducer toward the other transducer and so that a component of velocity of the ultrasonic waves is in one of the proximal and distal directions and parallel to the blood flow D. Also, as shown, coverings 465a-b may cover a respective transducer 460a-b. Moreover, in some embodiments of cannula 440, either the first or second transducers 460a-b may be replaced by a reflective surface.

In a method of use, when pump 30 is powered on, sensor elements 460a-b may also be powered on. Blood is urged through bore 446. First sensor element 460a, or second sensor elements 460b, emits ultrasonic waves with a component of velocity in a proximal or distal direction toward the other sensor element. The other sensor element receives the reflected waves and generates an electric signal indicative of the flow conditions of the blood flowing through bore 446. Such signals are transmitted through either conductor 464a or 464b down to cable 24 which may further transmit these signals to the signal processing apparatus and processed as discussed above.

Figure 5:
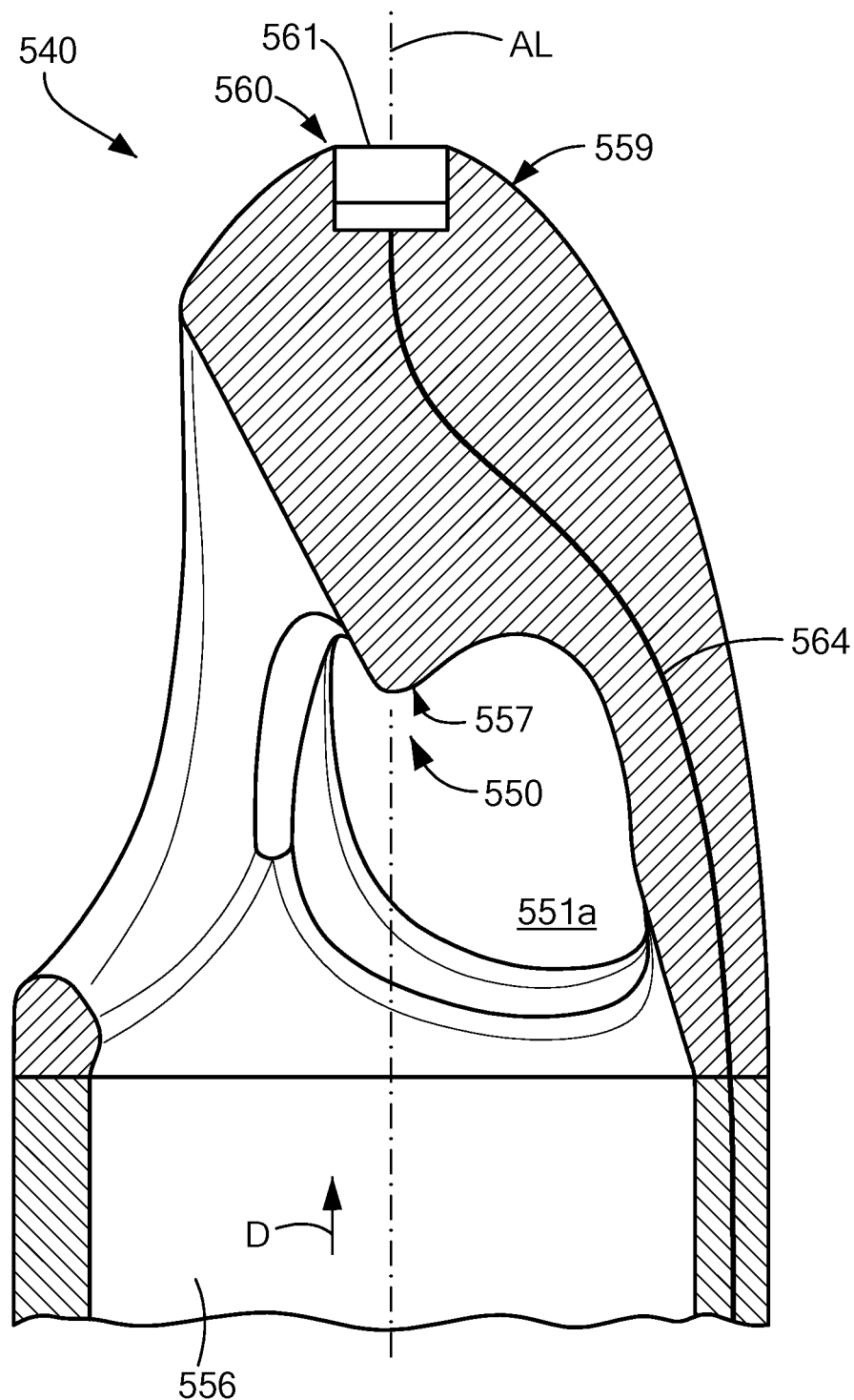
FIG. 5 is a sectional view of a cannula according to an even further embodiment of the present disclosure taken along a line intersecting an axis AL thereof.

In yet another embodiment, as depicted in FIG. 5, an outflow cannula 540 is similar to outflow cannula 40. In this regard, outflow cannula 540 includes a transverse wall 550 at a distal end thereof that is defined between an exterior portion 559 and an interior portion 557. Exterior portion 559 defines a distal extent of cannula 540 that is remote from pump 30. Additionally, interior portion 557 defines a proximal extent of bore 556. However, the difference between cannula 540 and cannula 40 is that a pressure sensor 560 is mounted to exterior portion 559 of transverse wall 550. Pressure sensor 560 may be similar to pressure sensor 260 and, as such, may include a sensing element 561 which is exposed to an environment external to cannula 540. This allows pressure sensor 560 to measure MAP downstream of outflow apertures 551a-c, Sensor 560 may be mounted to cannula 540 so that it is intersected by bore axis AL and generally faces a direction parallel to the blood flow D. Alternatively, sensor 560 may be mounted so that it is offset from axis AL and faces a direction transverse to the blood flow D.

In a method of use, when pump 30 is powered on, sensor 560 may also be powered on. Blood is urged through bore 556 of cannula 540 toward outlet apertures 551a-c. Blood is discharged from outlet apertures 551a-c into the mammalian subject's aorta 104. As blood flows about the exterior portion 559 and to the remainder of the mammalian subject's body, sensor 560 senses the pressure of the blood and generates signals indicative of such pressure, which may be MAP. Such signals are transmitted through conductor 564 down to cable 24 which may further transmit these signals to an external or internal controller which may further process the signals and store information derived therefrom for later retrieval or real-time display. Such information may allow a clinician and/or patient to continuously monitor prevailing conditions of blood as it is dispersed from the heart 100 to the remainder of the mammalian subject's body.

In the previously described embodiments, various sensing elements are mounted in either a transverse wall or a sidewall of an outflow cannula. However, it should be understood that a cannula, such as cannula 10, can include multiple sensing elements in multiple locations. For example, an outflow cannula can include a pressure sensor mounted to a transverse wall and one or more ultrasonic transducers or another pressure sensor mounted to its sidewall. In another example, an outflow cannula can include an ultrasonic transducer mounted to a transverse wall and one or more ultrasonic transducers or a pressure sensor mounted to its sidewall. Combining pressure sensors and ultrasonic transducers into a single outflow cannula can be beneficial in that measurements taken by the ultrasonic transducers can be used as reference data to recalibrate the pressure sensor as pressure sensors, in general, are susceptible to drift.

In addition, although the sensing elements, such as the ultrasonic transducers and pressure sensors described herein, are described as being electrically connected via a conductor that connects to a cable that powers the respective VAD, it should be understood that such sensing elements can be coupled to the signal processing apparatus by any other modality. For example, the sensors can be connected to miniature coils and can be activated by exposing the miniature coils to an electromagnetic field. In such an arrangement, the electrical signals from the sensors can be sent to the signal processing apparatus electromagnetically.

Although the invention herein has been described with reference to particular embodiments, it is to be understood that these embodiments are merely illustrative of the principles and applications of the present invention.

What is claimed is:

1. A ventricular assist device, comprising:
   a pump including a housing having an inlet, an outlet and a moveable element disposed in the housing for urging blood from the inlet to the outlet;
   an outflow cannula having a proximal end attached to the pump housing, a distal end remote from the pump housing, an interior bore having a longitudinal axis extending longitudinally and in communication with the outlet of the pump housing, a transverse wall extending transverse the longitudinal axis and at least one outlet aperture communicating with the interior bore remote from the pump housing; and
   at least one sensor mounted to the outflow cannula at the transverse wall and configured to detect a parameter of blood flowing at least one from the group consisting of through the outflow cannula and about an exterior of the outflow cannula.

2. The device of claim 1, wherein the transverse wall is disposed adjacent the distal end, and the at least one outlet aperture is disposed proximal to the transverse wall.

3. The device of claim 2, wherein the outflow cannula defines a tapered tip at its distal end, and the at least one outlet aperture includes a plurality of outlet apertures disposed in the tapered tip and spaced circumferentially around the axis of the interior bore.

4. The device of claim 1, wherein the transverse wall intersects the longitudinal axis of the interior bore.

5. The device of claim 2, wherein the at least one sensor includes at least one from the group consisting of a pressure sensor and a flow sensor.

6. The device of claim 3, wherein the transverse wall defines a terminal end of the bore.

7. The device of claim 6, wherein the transverse wall is contoured to direct blood flow in a direction toward the at least one outlet aperture.

8. The device of claim 1, wherein the transverse wall is defined between an interior portion that defines an extent of the interior bore and an exterior portion that defines an extent of outflow cannula remote from the pump.

9. The device of claim 8, wherein the sensor is mounted to at one of the interior portion and exterior portion.

10. The device of claim 1, further comprising an electrical conductor extending proximally and distally along the cannula, the at least one sensor being electrically connected to the electrical conductor.

11. The device of claim 1, further comprising a base member connected to the pump housing by an elongate member configured to form a gap therebetween.

12. The device of claim 1, wherein the outflow cannula further includes a sidewall surrounding the interior bore over at least a portion of its length, a least one said sensor being mounted to the sidewall.

13. The device of claim 1, wherein the at least one sensor includes at least one ultrasonic transducer mounted to the cannula, and wherein ultrasonic waves transmitted and received by the ultrasonic transducer, travel through the interior bore with a component of velocity in at least one of the proximal and distal directions.

14. The device of claim 13, wherein the at least one ultrasonic transducer includes two ultrasonic transducers spaced proximally and distally from one another.

15. The device of claim 13, wherein the at least one ultrasonic transducer includes a distal transducer mounted to the cannula adjacent the distal end thereof, and at least one of the pump and the cannula defines a reflective surface adjacent the proximal end of the cannula.

16. A ventricular assist device, comprising:
a pump including a housing having an inlet, an outlet and a moveable element disposed in the housing for urging blood from the inlet to the outlet;
an outflow cannula having a proximal end attached to the pump housing, a distal end remote from the pump housing, an interior bore in communication with the outlet of the pump housing, and at least one outlet aperture communicating with the interior bore remote from the pump housing;
at least one sensor mounted to the outflow cannula, the interior bore of the outflow cannula having an axis extending longitudinally, and the outflow cannula having a transverse wall extending transverse to the axis, the at least one sensor being mounted to the transverse wall and configured to detect a parameter of blood flowing at least one from the group consisting of through the outflow cannula and about an exterior of the outflow cannula, the at least one sensor includes at least one ultrasonic transducer mounted to the cannula and ultrasonic waves transmitted and received by the ultrasonic transducer, travel through the bore with a component of velocity in at least one of the proximal and distal directions; and
an electrical conductor extending proximally and distally along the cannula, the at least one sensor being electrically connected to the conductor.

* * * * *